United States Patent
Ji

(10) Patent No.: US 11,974,727 B2
(45) Date of Patent: May 7, 2024

(54) OPENING AND CLOSING UNIT AND ENDOSCOPE AND ENDOSCOPE SYSTEM INCLUDING THE SAME

(71) Applicant: TAEWOONG MEDICAL CO., LTD., Gimpo-si (KR)

(72) Inventor: Hyun Soo Ji, Seoul (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 59 days.

(21) Appl. No.: 17/750,798

(22) Filed: May 23, 2022

(65) Prior Publication Data
US 2023/0225604 A1 Jul. 20, 2023

(30) Foreign Application Priority Data
Jan. 14, 2022 (KR) .................. 10-2022-0006186

(51) Int. Cl.
*A61B 1/015* (2006.01)
*A61B 1/12* (2006.01)
*A61B 1/313* (2006.01)

(52) U.S. Cl.
CPC ............ *A61B 1/126* (2013.01); *A61B 1/3132* (2013.01)

(58) Field of Classification Search
CPC . A61B 1/00119; A61B 1/015; A61B 1/00068; A61B 1/00142
See application file for complete search history.

(56) References Cited

U.S. PATENT DOCUMENTS 10,743,746 B2 * 8/2020 Shats ..................... A61B 1/015

FOREIGN PATENT DOCUMENTS

| CN | 113855161 A | * | 12/2021 | |
| CN | 114365994 A | * | 4/2022 | |
| JP | 2001-231745 A | | 8/2001 | |
| JP | 2005-131163 A | | 5/2005 | |
| JP | 2006-175175 A | | 7/2006 | |
| JP | 2010-063483 A | | 3/2010 | |
| JP | 2015-198820 A | | 11/2015 | |
| JP | 2018-069094 A | | 5/2018 | |
| WO | WO-2018202268 A1 | * | 11/2018 | ......... A61B 1/00045 |
| WO | 2020/162565 A1 | | 8/2020 | |
| WO | WO-2020162565 A1 | * | 8/2020 | |

* cited by examiner

*Primary Examiner* — Michael J Carey
*Assistant Examiner* — Timothy Tuan Luu
(74) *Attorney, Agent, or Firm* — Bridgeway IP Law Group, PLLC; Jihun Kim

(57) ABSTRACT

An opening and closing unit includes a body that has a first hollow part penetrating through both ends thereof and an opening part communicating the first hollow part with an outside, and an opening and closing part that is inserted into the first hollow part to selectively open and close the opening part, has second hollow part formed therein, and has a through hole communicating with the second hollow part on one side thereof.

6 Claims, 6 Drawing Sheets

OPENING AND CLOSING UNIT AND ENDOSCOPE AND ENDOSCOPE SYSTEM INCLUDING THE SAME

BACKGROUND

1. Field of the Invention

The present disclosure relates to an apparatus and a system, and more particularly, to an opening and closing unit and an endoscope and an endoscope system including the same.

2. Discussion of Related Art

In general, surgery using an endoscope is conducted by inserting an endoscope equipped with a camera and a surgical tool through a small hole without making a large incision in a human body and then examining a patient's affected area through an image taken by the endoscope in the body. In particular, since endoscopic surgery originating from laparoscopic surgery has a smaller incision compared to abdominal surgery, the endoscopic surgery has the advantage of having a smaller scar area and less bleeding, resulting in speeding up a patient's recovery time after the surgery.

Since the conventional endoscope has a structure in which an insertion part inserted into a body and an operation part for controlling the insertion part are integrated, a plurality of conduits and guides penetrating through the inside of each part are built into the endoscope, and in particular, a tip of the insertion part inserted into the body is equipped with an imaging device such as an expensive CCD, the conventional endoscope has a problem in that it is difficult to separate only the insertion part from the operation part and replace the insertion part with a new insertion part. As a result, with the trend of strengthening the hygiene of medical endoscopes, various types of detachable endoscopes, which may connect and use the insertion part inserted into the body and the operation part operating the insertion part with each other or may separate and store the insertion part and the operation part from each other, are being used.

Meanwhile, in the case of discharging contaminants (e.g., blood) generated inside a patient's body during the endoscopic surgery to the outside, the contaminants are sucked and discharged by using a suction force generated from a suction device connected to the endoscope. In this case, the contaminants move to the outside of the endoscope through a discharge passage formed inside the endoscope, and the discharge passage is generally formed to pass through the inside of the operation part.

Accordingly, there may be a problem in that the inside of the operation part is contaminated due to the contaminants passing through the inside of the operation part through the discharge passage. However, since the inside of the operation part has a complicated structure in which various parts for flexural movement of the insertion part are coupled, it is difficult to clean the operation part when the inside of the operation part is contaminated, so, after the endoscopic surgery is finished, the operation part as well as the insertion part is being interchangeably used for the subsequent surgery. In addition, since the manufacturing and selling cost of the operation part is high due to its complicated internal structure, there is also a cost problem involved in replacing the operation part with a new operation part every time the endoscopic surgery is performed.

SUMMARY OF THE INVENTION

The present disclosure provides an opening and closing unit capable of preventing contaminants generated during an endoscopic surgery from flowing into an operation part of an endoscope to prevent the operation part from being contaminated, and an endoscope and an endoscope system including the same.

The technical problems to be achieved by the present disclosure are not limited to the technical problems described above, and other technical problems that are not described may be clearly understood by those with ordinary knowledge in the technical field to which the present disclosure belongs from the following description.

According to an embodiment of the present disclosure, an opening and closing unit may include a body that has a first hollow part penetrating through both end portions thereof and an opening part communicating the first hollow part with an outside, and an opening and closing part that is inserted into the first hollow part to selectively open and close the opening part, has second hollow part formed therein, and has a through hole communicating with the second hollow part on one side thereof.

The opening and closing part may be disposed inside the first hollow part to enable reciprocating linear movement along a longitudinal direction.

The through hole may selectively communicate with the opening part by the reciprocating linear movement of the opening and closing part.

The opening and closing part may move in one direction when the opening part is opened to dispose the through hole on the same line as the opening part so that the operation part and the through hole communicate with each other, and move in an opposite direction to the one direction when the opening part is closed to alternately dispose the through hole and the opening part so that the communication of the through hole and the opening part is released.

According to another embodiment of the present disclosure, an endoscope may include an insertion unit having one end inserted into a body, an operation unit that is coupled to the other end of the insertion unit, and operates the one end of the insertion unit to perform flexural movement using an operation module, a joint unit connected to one end portion of the operation unit, and the opening and closing unit described above which is disposed on the operation unit and selectively communicates the insertion unit and the joint unit.

According to a still another embodiment of the present disclosure, an endoscope system may include an endoscope, a suction unit that sucks and moves a contaminant generated during an endoscopic surgery, and a receiving unit that receives the contaminant moved by the suction unit and discharged to the outside.

The insertion unit may communicate with the suction unit by using a bypass formed to bypass the operation unit.

DETAILED DESCRIPTION OF EXEMPLARY EMBODIMENTS

Figure 1:
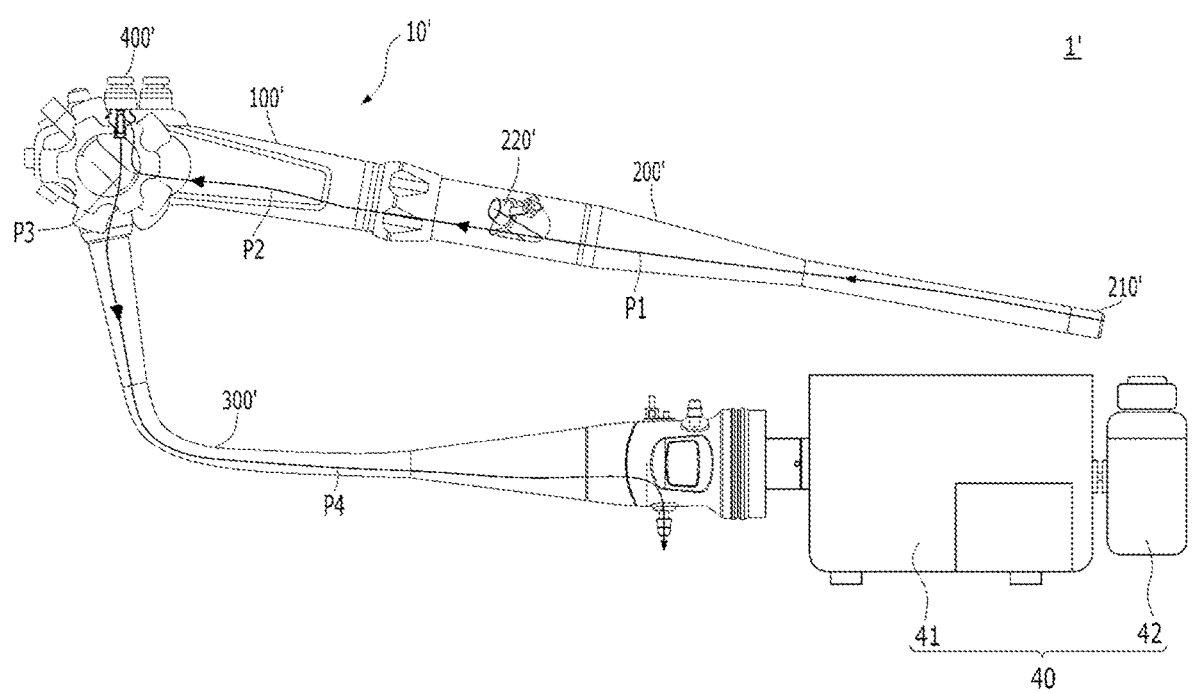
FIG. 1 is a diagram illustrating a conventional endoscope system.

Hereinafter, the present disclosure will be described with reference to the accompanying drawings. However, the present disclosure may be implemented in various different forms, and is not limited to exemplary embodiments described herein. In addition, in the drawings, portions unrelated to the description will be omitted to obviously describe the present disclosure, and similar reference numerals are attached to similar portions throughout the specification.

Throughout the present specification, when any one part is referred to as being "connected (joined, contacted, and coupled) to" another part, it means that any one part and another part are "directly connected to" each other or are "indirectly connected to" each other with the other part interposed therebetween. In addition, unless explicitly described to the contrary, "including" any component will be understood to imply the inclusion of other components rather than the exclusion of other components.

The terms used in the present specification are only used to describe specific embodiments, and are not intended to limit the present disclosure. Singular forms are intended to include plural forms unless the context clearly indicates otherwise. It should be further understood that terms "include" or "have" used in the present specification specify the presence of features, numerals, steps, operations, components, parts mentioned in the present specification, or combinations thereof, but do not preclude the presence or addition of one or more other features, numerals, steps, operations, components, parts, or combinations thereof.

Hereinafter, embodiments of the present disclosure will be described in detail with reference to the accompanying drawings.

FIG. 1 illustrates a conventional endoscope system.

Referring to FIG. 1, a conventional endoscope system 1' may include an endoscope 10', and a supply and suction unit 40. The endoscope 10' may include an endoscope operation part 100', an insertion part 200', a joint part 300', and an operation control part 400'. In this case, the insertion part 200' may be a part inserted into a patient's body during an endoscopic surgery, and the endoscope operation part 100' may be a part for operating flexural movement of the insertion part 200'. The joint part 300' is connected to an endoscope control and management system, and the operation control part 400' may be an operation part for selectively opening or closing a second pipe P2 to be described later.

The supply and suction unit 40 may include a pressure part 41 that generates a suction force for discharging saliva or foreign substances generated from an endoscopic surgery or generates a pressure required to supply liquid or gas, and a storage part 42 in which the liquid used for the endoscopic surgery is stored.

When contaminants (e.g., patient's blood) generated during the endoscopic surgery are sucked and discharged, the conventional endoscope system 1' uses the suction force generated from the pressure unit 41 to suck and move the contaminants, thereby discharging the contaminants to the outside of the patient's body and the endoscope 10'.

The sucked contaminants are discharged by moving along pipe parts P1, P2, P3, and P4 provided in the endoscope 10'. In this case, the pipe parts P1, P2, P3, and P4 may be formed by sequentially and continuously connecting a "first pipe P1" extending into the insertion part 200' from an opening part of an insertion end portion 210, a "second pipe P2" extending into the endoscope operation part 100' and connected to one side of the operation control part 400', a "third pipe P3" connected to the other side of the operation control part 400' and extending toward the joint part 300', and a "fourth pipe P4" extending into the joint part 300' and connected to a discharge part.

In this case, when the contaminants sucked through the opening part pass through the first pipe P1 and pass through the second pipe P2, as the second pipe P2 extends through the inside of the endoscope operation part 100', the contaminants may flow into the inside of the endoscope operation part 100', thereby causing a problem in that the inside of the endoscope operation part 100' is contaminated. In this case, since the endoscope operation part 100' is configured to have a complicated internal structure for the flexural movement of the insertion part 200', there is a problem that it is difficult to clean the endoscope operation part 100' when the inside of the endoscope operation part 100' is contaminated.

Figure 2:
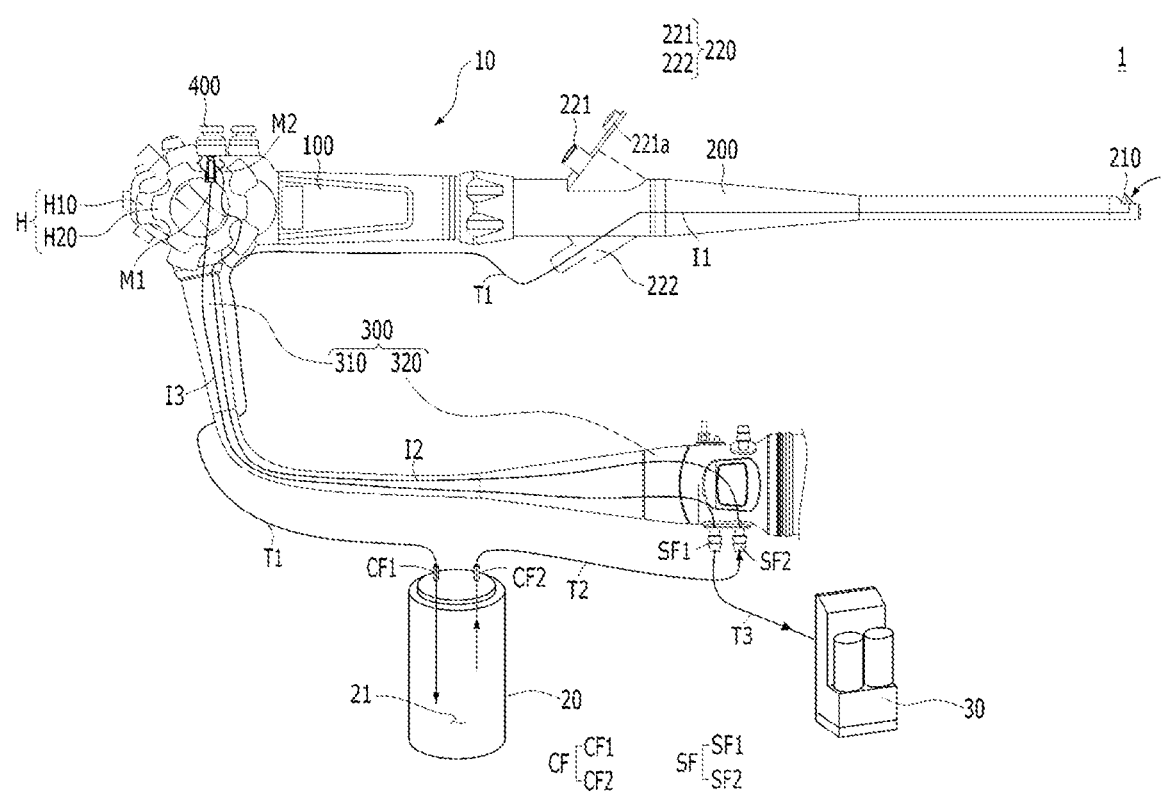
FIG. 2 is a diagram illustrating an endoscope system according to an embodiment of the present disclosure.

FIG. 2 illustrates an endoscope system according to an embodiment of the present disclosure.

Referring to FIG. 2, the endoscope system 1 according to the present disclosure may be a system for performing an endoscopic surgery on a patient and discharging contaminants (e.g., blood) generated during the surgery to the outside of the body. In this case, the endoscope system 1 may include an endoscope 10, a receiving unit 20, and a suction unit 30.

The endoscope 10 may include an operation unit 100, an insertion unit 200, and a joint unit 300, and an opening and closing unit 400. In the present specification, an embodiment of a "detachable endoscope" in which the insertion unit 200 is detachably coupled to the operation unit 100 will be mainly described, but is not limited thereto.

The operation unit 100 is a part operated by a user to control the operation of the insertion unit 200, and may include an operation module H. In this case, the operation module H may include a first operation part H10 and a second operation part H20.

The detachable insertion unit 200 may be selectively connected to one end of the operation unit 100. In the state in which the insertion unit 200 is coupled to the operation unit 100, a user may rotate the first operation part H10 in left and right directions to flex a tip (hereinafter, insertion end portion) of the insertion unit 200 in upward and downward directions, or rotate the operation part H20 in the left and right directions to flex the above-described insertion end portion in the left and right directions.

The operation unit 100 may include intermediate pipe parts M1 and M2. As an embodiment, a pair of intermediate pipe parts M1 and M2 may be provided and disposed inside the operation unit 100. In this case, the pair of intermediate pipe parts will be referred to as a first intermediate pipe part M1 and a second intermediate pipe part M2 for convenience of description. The first intermediate pipe part M1 and the second intermediate pipe part M2 are disposed between the opening and closing unit 400 and the joint unit 300 to communicate the opening and closing unit 400 and the joint unit 300 each other, which will be described later.

A portion (i.e., insertion end portion) of the insertion unit 200 may be inserted into a body during the endoscopic surgery. In this case, the insertion end portion may be an end portion opposite to an end portion coupled to the operation unit 100 among both end portions of the insertion unit 200. The insertion end portion may be provided with an illumination imaging part that includes a light source illuminating a body and an image sensor capturing the body.

The insertion unit 200 may include an auxiliary connection unit 220 that provides a passage through which surgical equipment and a suction nozzle used for the endoscopic surgery are inserted into the endoscope 10. In this case, the insertion unit 200 may include a first pipe part I1. The first pipe part I1 may be disposed inside the insertion unit 200. One end of the first pipe part I1 may communicate with the outside of the endoscope 10 through the insertion end portion of the insertion unit 200, and the other end of the first pipe part I1 may extend toward the other end (e.g., the opposite end portion of the insertion end portion) of the insertion unit 200 to be connected to the auxiliary connection unit 220.

As an embodiment, the auxiliary connection unit 220 may include a pair of auxiliary insertion parts 221 and 222. In this case, the pair of auxiliary insertion parts 221 and 222 is each provided with a hollow part communicating with an inner space of the insertion unit 200, and these hollow parts may be connected to the first pipe part I1.

In this case, a tip of equipment for the endoscopic surgery may be inserted into the insertion unit 200 through a "first auxiliary insertion part 221" which is one of the pair of auxiliary insertion parts. In this case, a user may operate the operation module H before or after inserting the surgical equipment to move the insertion end portion 210 of the insertion unit 200 to a surgical target part located inside a patient's body. Accordingly, the tip of the surgical equipment inserted into the insertion unit 200 may move along the first pipe part I1 and move toward the insertion end portion 210, and may be drawn out to the outside of the endoscope 10 through the opening part formed in the insertion end portion 210. As a result, the surgical equipment may be guided to a surgical target location inside a patient's body to perform surgery.

In addition, a tip of a first tube T1 to be described later may be inserted into the insertion unit 200 through a "second auxiliary insertion part 222" which is the other one of the pair of auxiliary insertion parts. In this case, the other end of the first tube T1 may be connected to the receiving unit 20. In this case, the contaminants generated during the endoscopic surgery may move to the receiving unit 20 through the first pipe part I1 and the first tube T1 communicating with the first pipe part I1.

The joint unit 300 may be connected to the endoscope management and control part of the detachable endoscope 10. Here, the endoscope management and control part may include the receiving unit 20 and the suction unit 30 as described above, which will be described in detail below.

The joint unit 300 may be disposed between the operation unit 100 and the endoscope control unit to connect the operation unit 100 and the endoscope control part. As an embodiment, a tip 310 of the joint unit 300 may be connected to the operation unit 100, and a rear end portion 320 of the joint unit 300 may be connected to the endoscope control part.

The joint unit 300 may be provided with second pipe parts I2 and I3 penetrating from the tip 310 to the rear end portion 320 therein.

In one embodiment, the second pipe parts I2 and I3 may be provided in a pair. In this case, when the joint unit 300 is coupled to the operation unit 100, one end of the "2-1th pipe part I2," which is any one of the pair of second pipe parts, may be connected to the second intermediate pipe part M2. In addition, one end portion of the "2-2th pipe part I3," which is the other one of the pair of second pipe parts, may be connected to the first intermediate pipe part M1. In this case, the other end of "the 2-1th pipe part I2" may communicate with the receiving unit 20 via a second tube T2. The other end of the "2-2 pipe part I3" may be connected to the suction unit 30 via a third tube T3.

The opening and closing unit 400 may selectively communicate the insertion unit 200 and the joint unit 300 with each other when the insertion unit 200 and the joint unit 300 are coupled to the operation unit 100, which will be described in detail below.

Figure 3:
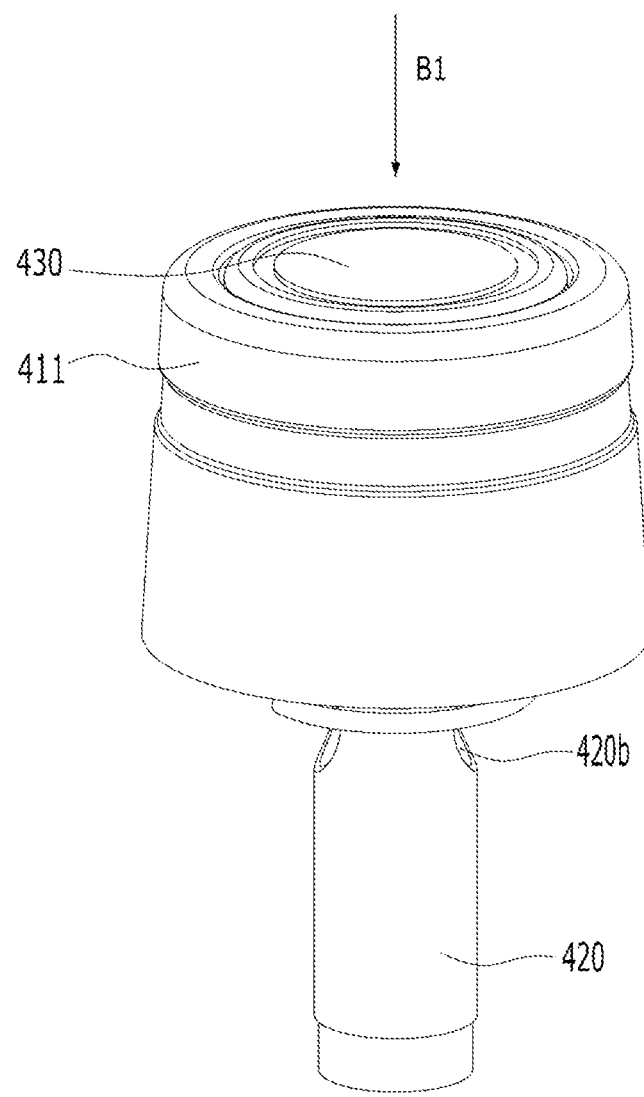
FIG. 3 is a perspective view illustrating a portion of an opened opening and closing unit which is provided in an endoscope according to an embodiment of the present disclosure.
Figure 4:
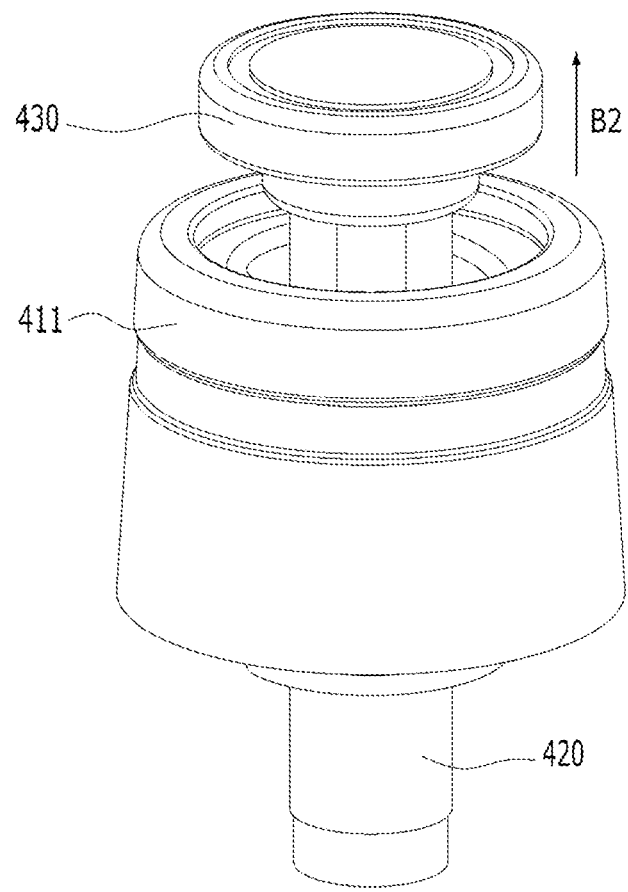
FIG. 4 is a perspective view illustrating a portion of the closed opening and closing unit which is provided in the endoscope according to the embodiment of the present disclosure.
Figure 5:
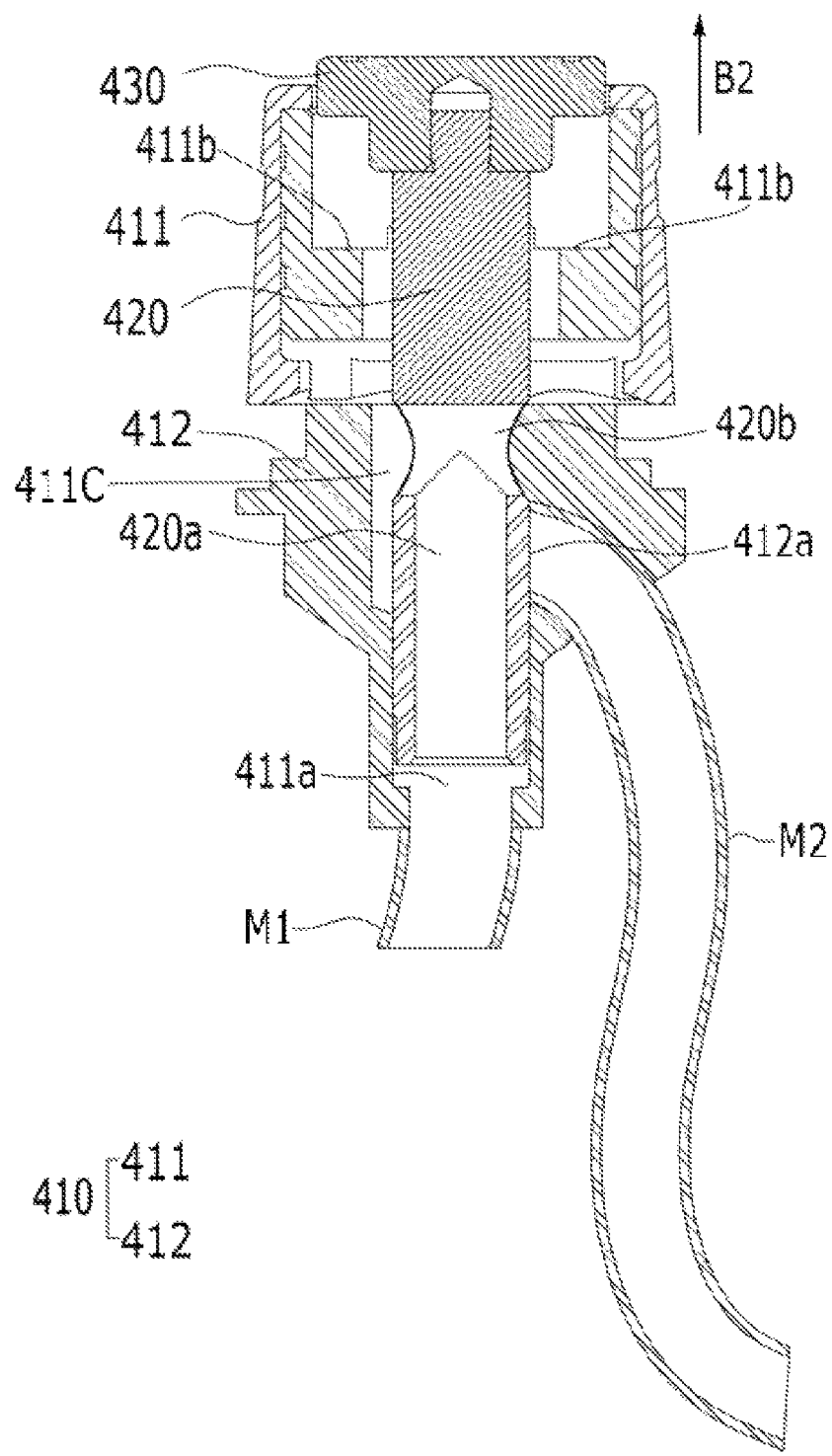
FIG. 5 is a traverse cross-sectional view illustrating the opened opening and closing unit which is provided in the endoscope according to the embodiment of the present disclosure.
Figure 6:
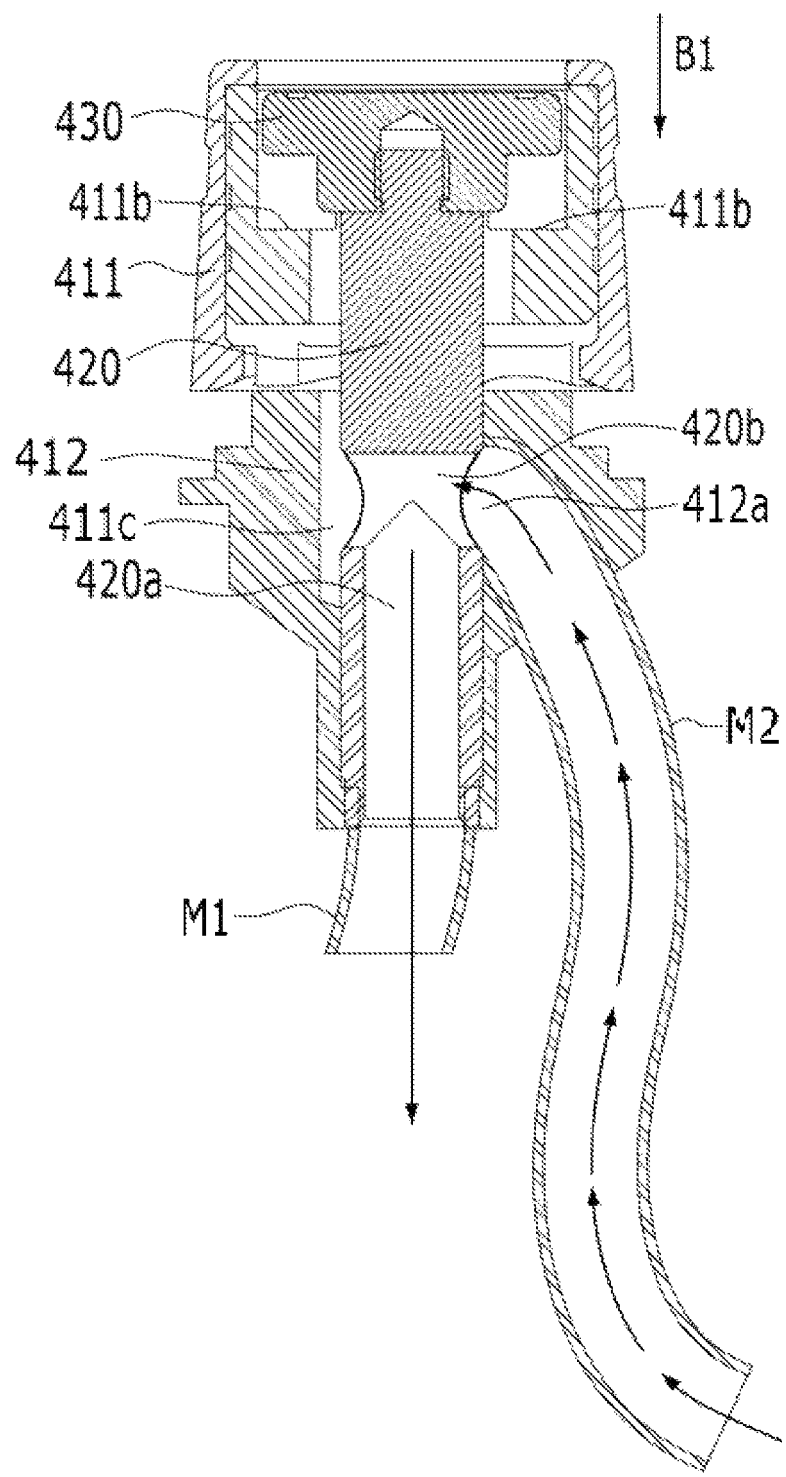
FIG. 6 is a traverse cross-sectional view illustrating the closed opening and closing unit which is provided in the endoscope according to the embodiment of the present disclosure.

FIG. 3 is a perspective view illustrating a portion of the opened opening and closing unit provided which is provided in the endoscope according to an embodiment of the present disclosure, FIG. 4 is a perspective view illustrating a portion of the closed opening and closing unit which is provided in the endoscope according to an embodiment of the present disclosure. FIG. 5 is a transverse cross-sectional view illustrating the opened opening and closing unit which is provided in the endoscope according to the embodiment of the present disclosure, and FIG. 6 is a transverse cross-sectional view illustrating the closed opening and closing unit which is provided in the endoscope according to the embodiment of the present disclosure.

Referring to FIGS. 3 to 6, the opening and closing unit 400 according to the embodiment of the present disclosure may include a body 410, an opening and closing part 420, and an operation part 430.

The body 410 is a part in which the opening and closing part 420 is disposed, and may guide the opening and closing movement of the opening and closing part 420.

The body 410 may include an upper end portion 411 and a lower end portion 412. In this case, the upper end portion 411 may be a portion including an end portion disposed on the upper side with respect to the vertical direction of the drawing, and the lower end portion 412 may be a portion including an end portion disposed at the lower side. In an embodiment, the upper end portion 411 and the lower end portion 412 may be configured as separate structures from each other. In this case, the body 410 may be formed by coupling the upper end portion 411 and the lower end portion 412.

The body 410 may have a first hollow part 411a therein. The first hollow part 411a may be formed to penetrate from the upper end portion 411 to the lower end portion 412 along the vertical direction.

In this case, the body 410 may include an opening part 412a for communicating the first hollow part 411a with the outside. In an embodiment, the opening part 412a may be disposed on the side of the lower end portion 412. In this case, the opening part 412a may be formed by penetrating through the side surface of the lower end portion 412 along a direction (e.g., radial direction) perpendicular to a longitudinal direction (or vertical direction in the drawing) of the body 410. Through the opening part 412a, the first hollow part 411a may be in communication with the outside of the body 410.

The first hollow part 411a may have a stepped portion 411b. The step portion 411b may be disposed on the inner side of the upper end portion 411 to define the opening/closing movement range of the operation part 430, which will be described below.

The opening and closing part 420 may selectively open and close the above-described opening part 412a to control the communication state with the outside of the first hollow part 411a. The opening and closing part 420 may be, for example, a cylindrical bar. In this case, the opening and closing part 420 may be formed to have a diameter equal to or similar to an inner diameter of the first hollow part 411a.

The opening and closing part 420 may be inserted into and disposed in the first hollow part 411a. In this case, the opening and closing part 420 may be disposed to enable reciprocating linear movement (hereinafter, opening and closing movement) along a downward direction B1 and an upward direction B2 while being inserted into the first hollow part 411a.

The opening and closing part 420 may have a second hollow part 420a therein. The second hollow part 420a may be formed to extend upward from the lower end portion of the opening and closing part 420. In this case, the opening and closing part 420 may have a through hole 420b for communicating the second hollow part 420a with the outside.

In an embodiment, the through hole 420b may be formed to penetrate through the side surface of the opening and closing part 420. More specifically, the through hole 420b may be formed to penetrate through the side surface of the opening and closing part 420 along the direction (e.g., radial direction) perpendicular to the longitudinal direction (or vertical direction in the drawing) of the opening and closing part 420b. Accordingly, the through hole 420b may be in a state in which both end portions (hereinafter, opened end portion) are opened along a width direction (or the longitudinal direction of the through hole 420b) of the opening and closing part 420. Through the through hole 420b, the second hollow part 420a may selectively communicate with the first hollow part 411a or the opening part 412a.

The operation part 430 may be a part for operating the opening and closing movement of the opening and closing part 420. In an embodiment, the operation part 430 may be connected to the opening and closing part 420. Specifically, the upper end portion of the operation part 430 may be exposed to the outside through the upper opening part of the first hollow part 411a, and the lower end portion of the operation part 430 may be connected with the upper end portion of the opening and closing part 420 to reciprocate in the upward and downward directions B1 and B2 together with the opening and closing part 420.

As exemplarily illustrated in FIGS. 3 and 5, a user may move the opening and closing part 420 in the downward direction B1 by pressing the upper surface of the operation part 430. As such, the opening and closing part 420 may move in the downward direction B1 so that the through hole 420b is disposed on the same line as the opening part 412a, thereby communicating the through hole 420b and the opening part 412a with each other. In this case, among both opened end portions of the through hole 420b, the opened end portion facing the opening part 412a may communicate with the opening part 412a. As a result, the second hollow part 420a may communicate with the second intermediate pipe part M2 through the through hole 420b and the opening part 412a, and thus, may be in a state (hereinafter, an opened state) in which a fluid may move into the second hollow part 420a through the second intermediate pipe part M2.

In an embodiment, the first hollow part 411a may have an inner groove part 411c depressed outwardly in a radial direction from its inner surface. In this case, the inner groove part 411c may be disposed on an inner surface opposite to the opening part 412a. The inner groove part 411c may at least partially communicate with an opened end portion located on the opposite side of the opening part 412a among both opened end portions of the through hole 420b.

Meanwhile, the operation part 430 may have a larger diameter than the opening and closing part 420. The operation part 430 may be in contact with the stepped portion 411b when the operation part 430 moves by a predetermined distance in the downward direction B1 by the user's pressure. In this case, the operation part 430 is blocked by the stepped portion 411b, and thus, may not be able to move further in the downward direction B1. As such, the stepped part 411b may define the opening/closing movement range of the operation part 430 by limiting the movement distance in the downward direction B1 of the operation part 430.

As exemplarily illustrated in FIGS. 4 and 6, a user may release the above-described "opened state" by removing a force applied to the operation part 430.

For example, when stopping the fluid from flowing into the second hollow part 420a, the user may remove the force applied to the upper surface of the operation part 430 to move the operation part 430 back in the upward direction B2. Accordingly, the through hole 420b may move in the upward direction B2 to be positioned above the opening part 412a, so the through hole 420b and the opening part 412a may be disposed in a "alternate state."

In this case, the open end disposed on the opening part 412a side among both opened end portions of the through hole 420b, which is in the "alternate state", may be closed by the inner surface of the lower end portion 412 of the body 410, and the opening part 412a may be closed by the outer surface of the opening and closing part 420. As a result, the through hole 420b is isolated from the opening part 412a, and thus, may be in a state (hereinafter, a closed state) in which the fluid may not move into the second hollow part 420a through the second intermediate pipe part M2.

In an embodiment, the operation part 430 may include an elastic member (not illustrated). The elastic member may be disposed between the lower surface of the operation part 430 and the stepped portion 411b of the body 410. The elastic member may be compressively deformed when the operation part 430 is pressed in the downward direction B1, and when the force applied to the operation part 430 is removed, may supply an elastic restoring force in the upward direction B2.

In this case, as the pressure by the user is removed, the elastic member may apply the elastic restoring force in the upward direction B2 to move the operation part 430 in the upward direction B2. In this case, after the pressure by the user is removed, when a predetermined time elapses, the operation part 430 may return to its original position.

The opening and closing unit 400 may be disposed in the operation unit 100. In an embodiment, the opening and closing unit 400 may be disposed on one side of the operation unit 100. In this case, the one side of the operation unit 100 may be a side adjacent to the operation module H. In this way, by disposing the opening and closing unit 400 in a position adjacent to the operation module H, the user of the endoscope 10 may simultaneously or separately perform the flexural movement of the insertion unit 200 and the opening and closing movement of the opening and closing unit 400 by using only one hand.

More specifically, in the opening and closing unit 400, the upper end 411 of the body 410 and the operation unit 430 may protrude to the outside of the operation unit 100, and the lower end portion 412 of the body 410 may be inserted into the operation unit 100. In this case, while being disposed inside the operation unit 100, the opening part 412a may be connected to the second intermediate pipe part M2, and the first hollow part 411a may be connected to the first intermediate pipe part M1.

Referring back to FIG. 2, the receiving unit 20 may be a part in which the contaminants generated during the endoscopic surgery are discharged and received. In this case, the contaminants may be, for example, blood generated during the endoscopic surgery. In an embodiment, the receiving unit 20 may be a cylindrical tank having an inner space 21 therein, but the present disclosure is not limited thereto, and the receiving unit 20 may have a shape different from the cylindrical shape.

The receiving unit 20 may have a connection part CF. In an embodiment, a pair of connection parts CF may be provided. In this case, the pair of connection parts CF may be disposed to communicate with the inner space 21 of the receiving unit 20. In this case, a first tube T1 may be connected to any one CF1 of the pair of connection parts CF, and a second tube T2 may be connected to the other one CF2 of the pair of connection parts CF.

The suction unit 30 may suck the contaminants generated during the endoscopic surgery and discharge the sucked contaminants to the outside of the patient's body and the endoscope 10. The suction unit 30 may be, for example, a suction machine that generates a suction force through a pump and sucks saliva or foreign substances through an inlet and discharges the saliva or foreign substances.

The suction unit 30 may be connected to the endoscope 10 via a third tube T3. Specifically, one end of the third tube T3 may be connected to the suction unit 30. The other end of the third tube T3 may communicate with the 2-2th pipe part I3 through the suction connection part SF of the joint unit 300. In this case, the 2-2th pipe part I3 may be connected to the first intermediate pipe part M1 by extending through the inside of the joint unit 300.

Using the above-described endoscope system 1, a method of sucking and removing contaminants during endoscopic surgery may be as follows.

First, the endoscope 10 in the state in which the insertion unit 200 and the joint unit 300 are connected to the operation unit 100 may be connected to the receiving unit 20 and the suction unit 30.

In this case, the first pipe part I1 may be connected to the inner space 21 of the receiving unit 20 via the first tube T1. Specifically, one end of the first tube T1 may be inserted into the second auxiliary insertion part 222 provided in the insertion unit 200 to be connected to the first pipe part I1. In this case, the other end of the first tube T1 may be drawn out of the second auxiliary insertion part 222 and may extend toward the receiving unit 20 while forming a "bypass" bypassing the operation unit 100. The other end of the first tube T1 may be connected to any one CF1 of the pair of connection parts to communicate with the inner space 21 of the receiving unit 20. Accordingly, the first tube T1 may communicate with the insertion unit 200 and the receiving unit 20 through the "bypass" formed outside the operation unit 100 without passing through the inner space 21 of the operation unit 100. At the same time, the first tube T1 may be connected to the first intermediate pipe part M1 to communicate with the first hollow part 411a of the opening and closing unit 400.

In addition, one end of the second intermediate pipe part M2 may be connected to the opening part 412a provided in the opening and closing unit 400, and the other end of the second intermediate pipe part M2 may be connected to one end of the 2-1th pipe part I2 provided inside the joint unit 300. In this case, the other end of the 2-1th pipe part I2 may be connected to the second tube T2 through any one of the pair of suction connection parts SF, and the second tube T2 may be connected to the other one CF2 of the pair of connection parts. As such, the opening part 412a of the opening and closing unit 400 may communicate with the inner space 21 of the receiving unit 20 through the second intermediate pipe part M2, the 2-1th pipe part I2, and the second tube T2 sequentially connected thereto. The first pipe part I1 connected to the first tube T1 may extend past the inside of the insertion unit 200 and communicate with the outside of the endoscope 10 through the opening part of the insertion end portion 210.

Accordingly, in the opening part of the insertion end portion 210, a "first flow path part 210-I1-T1-CF1-21" leading to the space 21 through the first tube T1 forming a circuit outside the operation unit 100 past the first pipe part I1 inside the insertion unit 200 may be formed. In the inner space 21 of the receiving unit 20, a "second flow path part 21-CF2-T2-SF2-I2-M2-412" leading to the opening part 412a of the opening and closing unit 400 through the second intermediate pipe part M2 past the second tube T2 and the 2-1th pipe part I2 sequentially connected thereto may be formed. In the second hollow part 420a of the opening and closing unit 400, a "third flow path part 420a-M1-I3-SF1-T3" leading to the suction unit 30 through the third tube T3 past the first intermediate pipe part M1 and the 2-2th pipe part I3 connected thereto may be formed.

Next, a user may insert at least a portion (e.g., insertion end portion 210 and its peripheral portion) of the insertion unit 200 into the patient's body. In this case, by using the operation module H, the user flexes the insertion end portion 210 in the up-down and/or left-right directions, so that the insertion end portion may be positioned in a surgical target part inside the patient's body. Thereafter, the user may perform endoscopic surgery by moving the surgical equipment to the surgical target part through the first auxiliary insertion part 221 and the first pipe part I1 communicating therewith. During this surgery, contaminants such as blood may occur in the surgical target part and its peripheral portion.

Next, the suction unit 30 may generate a suction force by performing a suction operation. In this case, the user may selectively press the operation part 430 of the opening and closing unit 400 to transmit the suction force to the insertion end portion 210. Meanwhile, the user may draw out the surgical equipment from the insertion unit 200 prior to the suction of the contaminants, and then may seal the first auxiliary insertion unit 221 by using a cap 211a.

In the case of discharging the contaminants generated during the endoscopic surgery to the outside of the body, the user may press the operation part 430 to move the opening and closing part 420 in the downward direction B1. As a result, the through hole 420b may communicate with the opening part 412a and may be in the "opened state," and thus, the third flow path part 420a-M1-I3-SF1-T3 may be connected to the second flow path part 21-CF2-T2-SF2-I2-M2-412 and the inner space 21 of the receiving unit 20. Accordingly, the third flow path part 420a-M1-I3-SF1-T3 may also communicate with the first flow path part 210-I1-T1-CF1-21 forming the "bypass," and as a result, may communicate with the surgical target part inside the patient's body and its peripheral portion through the opening part of the insertion end portion 210.

In this case, by the suction action of the suction unit 30, the contaminants may be sucked through the opening part of the insertion end portion 210, pass through the first flow path part 210-I1-T1-CF1-21, and may be sucked and moved towards the receiving unit 20. The contaminants that move in this way may be discharged into the inner space 21 of the receiving unit 20. As such, by the user's operation, the contaminants that are sucked and moved may pass through the "bypass" formed outside the operation unit 100 and may be received in the receiving unit 20, thereby preventing the contaminants from flowing into the operation unit 100 during the endoscopic surgery and preventing the inside of the operation unit 100 from being contaminated due to the contaminants.

As another example, when the discharge of the contaminants is completed or it is no longer necessary to discharge the contaminants, the user stops pressing the operation part 430 to move the opening and closing part 420 in the upward direction B2 and make the opening and closing part 420 return to its original position. Thereby, the state in which the through hole 420b communicates with the opening part 412a is released, and thus, the through hole may be in the "closed state." As a result, the second flow path part 21-CF2-T2-SF-I2-M2-412 is closed, so the suction force generated from the suction unit 30 is not transmitted to the first flow path part 210-I1-T1-CF1-21 and the insertion end portion 210, thereby stopping the suction action of the contaminants through the opening part of the insertion end portion 210.

In this case, as the operation part 430 moves in the upward direction B2, the first hollow part 411a may communicate with the outside through a "separation space between the operation part 430 and the upper end portion 411 of the body 410." As a result, when the suction operation of the suction unit 30 continues, air may be sucked through the "separation space" instead of the closed opening part 412a.

As described above, according to the opening and closing unit 400 and the endoscope 10 and the endoscope system 1 including the same in accordance with the embodiments of the present disclosure, by pressurizing or depressurizing an operation part of the opening and closing unit, it is possible to simply and easily control suction of contaminants or interruption of suction of the contaminants. In addition, by connecting the insertion unit 200 and the receiving unit 20 through the bypass formed by bypassing the operation unit 100, it is possible to prevent the sucked contaminants from flowing into the operation unit 100, and as a result, to solve the cleaning problem of the operation unit 100 and reuse the operation unit 100.

According to an opening and closing unit and an endoscope and an endoscope system including the same in accordance with embodiments of the present disclosure, by pressurizing or depressurizing an operation part of the opening and closing unit, it is possible to simply and easily control suction of contaminants or interruption of suction of the contaminants. In addition, by connecting an insertion unit and a receiving unit through a bypass formed by bypassing the operation unit, it is possible to prevent sucked contaminants from flowing into the operation unit, and as a result, solve a cleaning problem of the operation unit and reuse the operation unit.

The effect of the present disclosure is not limited to the above effects, and should be understood to include all effects that can be inferred from the detailed description of the present disclosure or the composition of the disclosure described in the claims.

It can be understood that the above description of the disclosure is for illustrative purposes only, and those skilled in the art to which the disclosure belongs can easily convert the disclosure into another specific form without changing the technical ideas or essential features of the disclosure. Therefore, it should be understood that the above-mentioned embodiments are exemplary in all aspects but are not limited thereto. For example, each component described as a single type may be implemented in a distributed manner, and similarly, components described as distributed may be implemented in a combined form.

It is to be understood that the scope of the present disclosure will be defined by the claims rather than the above-mentioned description and all modifications and alternations derived from the claims and their equivalents are included in the scope of the present disclosure.

What is claimed is:

1. An endoscope system, comprising:
   an endoscope;
   an air pump configured to suck and move a contaminant generated during an endoscopic surgery; and
   a reservoir configured to receive the contaminant moved by the air pump,
   wherein the endoscope comprises:
   an insertion unit having an insertion end portion configured to be inserted into a human body;
   an operation unit coupled to the insertion unit and configured to operate the insertion end portion of the insertion unit to perform flexural movement by using an operation module;
   a joint unit connected to one end of the operation unit; and
   a valve disposed on the operation unit and configured to selectively communicate the insertion unit and the joint unit with each other,
   wherein, starting from a distal opening of the insertion end portion, a first flow path leading to a space of the reservoir through a first tube forming a circuit outside the operation unit past a first pipe part inside the insertion unit is formed; starting from an inner space of the reservoir, a second flow path leading to an opening part of the valve through a second intermediate pipe part past a second tube and a first connecting pipe part sequentially connected thereto is formed; and starting from a second hollow part of the valve, a third flow path leading to the air pump through a third tube past a first intermediate pipe part and a second connecting pipe part connected thereto is formed.

2. The endoscope system of claim 1, wherein the insertion unit communicates with the air pump through bypassing the operation unit.

3. The endoscope system of claim 1, wherein the valve comprises:
   a body that has a first hollow part penetrating through both end portions thereof and the opening part communicating the first hollow part with an exterior of the body; and
   an opening and closing part that is inserted into the first hollow part to selectively open and close the opening part, has the second hollow part formed therein, and has a through hole communicating with the second hollow part on one side thereof.

4. The endoscope system of claim 3, wherein the opening and closing part is disposed inside the first hollow part to enable reciprocating linear movement along a longitudinal direction.

5. The endoscope system of claim 4, wherein the through hole selectively communicates with the opening part by the reciprocating linear movement of the opening and closing part.

6. The endoscope system of claim 5, wherein the opening and closing part moves in a first direction to align the through hole with the opening part to allow communication therebetween, and moves in a second direction to misalign the through hole and the opening part to discontinue the communication.

\* \* \* \* \*